(12) United States Patent
Zhukovsky et al.

(10) Patent No.: US 10,066,015 B2
(45) Date of Patent: Sep. 4, 2018

(54) CD3 BINDING DOMAINS

(71) Applicant: Affimed GmbH, Heidelberg (DE)

(72) Inventors: Eugene Zhukovsky, Mannheim (DE); Melvyn Little, St. Peter-Ording (DE); Stefan Knackmuss, Plankstadt (DE); Uwe Reusch, Maikammer (DE); Kristina Ellwanger, Heidelberg (DE); Ivica Fucek, Hamburg (DE); Michael Weichel, Bischofsheim (DE); Markus Eser, Düsseldorf (DE); Fionnuala McAleese-Eser, Düsseldorf (DE)

(73) Assignee: Affirmed GmbH, Heidelberg (DE)

( * ) Notice: Subject to any disclaimer, the term of this patent is extended or adjusted under 35 U.S.C. 154(b) by 199 days.

(21) Appl. No.: 14/820,462

(22) Filed: Aug. 6, 2015

(65) Prior Publication Data
US 2016/0039934 A1 Feb. 11, 2016

(30) Foreign Application Priority Data

Feb. 11, 2015 (EP) .................................... 15154772

(51) Int. Cl.
*A61K 39/395* (2006.01)
*C07K 16/28* (2006.01)
*C07K 16/30* (2006.01)

(52) U.S. Cl.
CPC ...... *C07K 16/2809* (2013.01); *C07K 16/2863* (2013.01); *C07K 16/2878* (2013.01); *C07K 16/30* (2013.01); *C07K 2317/24* (2013.01); *C07K 2317/31* (2013.01); *C07K 2317/33* (2013.01); *C07K 2317/56* (2013.01); *C07K 2317/567* (2013.01); *C07K 2317/626* (2013.01); *C07K 2317/73* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 8,101,722 | B2 | 1/2012 | Kufer et al. |
| 9,212,225 | B1 * | 12/2015 | Ellwanger .......... C07K 16/2803 |
| 2013/0129730 | A1 | 5/2013 | Kufer et al. |
| 2014/0242077 | A1 | 8/2014 | Choi et al. |
| 2014/0377270 | A1 | 12/2014 | Moore et al. |

FOREIGN PATENT DOCUMENTS

| WO | 2012162067 A2 | 11/2012 |
| WO | 2014106015 A2 | 7/2014 |
| WO | 2015018527 A1 | 2/2015 |

OTHER PUBLICATIONS

Vajdos et al. (J Mol Biol. Jul. 5, 2002;320(2):415-28).*
Colman (Research in Immunology, 145:33-36, 1994).*
Rudikoff et al. (Proc. Natl. Acad. Sci. USA, 79: 1979-1983, Mar. 1982).*
Brown et al. (J Immunol. May 1, 1996;156(9):3285-91).*
Bedouelle et al. (FEBS J. Jan. 2006;273(1):34-46).*

* cited by examiner

*Primary Examiner* — Zachary S Skelding
(74) *Attorney, Agent, or Firm* — Perkins Coie LLP; Viola T. Kung

(57) ABSTRACT

The invention relates to a humanized CD3 binding site, which comprises (a) a variable heavy chain domain (VH) as depicted in SEQ ID NO:8 and a variable light chain domain (VL) as depicted in SEQ ID NO:3; or (b) a variable heavy chain domain (VH) as depicted in SEQ ID NO:9 and a variable light chain domain (VL) as depicted in SEQ ID NO:4, or c) a variable heavy chain domain (VH) as depicted in SEQ ID NO:7 and a variable light chain domain (VL) as depicted in SEQ ID NO:2; or (d) a variable heavy chain domain (VH) as depicted in SEQ ID NO:6 and a variable light chain domain (VL) as depicted in SEQ ID NO:1. The CD3 binding sites have an increased stability, while the binding affinity has been retained due to mutations at positions VH111 and VL49.

11 Claims, 4 Drawing Sheets

Specification includes a Sequence Listing.

CD3 BINDING DOMAINS

CROSS-REFERENCE TO RELATED APPLICATIONS

This application claims the priorities of PCT Patent Application No. PCT/EP2014/002177, filed Aug. 7, 2014 and European Patent Application No. EP15154772.6, filed Feb. 11, 2015, each of which is incorporated in its entirety herein by reference.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Aug. 6, 2015, and a size of 37 kilobytes. The Sequence Listing filed via EFS-Web is part of the specification and is hereby incorporated in its entirety by reference herein.

TECHNICAL FIELD

The invention relates to antigen binding proteins comprising a new CD3 binding site. In particular, the invention relates to multispecific antigen binding proteins. The new CD3 binding site comprises humanized VH and VL domains.

BACKGROUND OF THE INVENTION

CD3 antigen is associated with the T-cell receptor complex on T-cells. Multispecific antigen binding proteins having specificity to CD3 and an antigen of a target cell can trigger the cytotoxic activity of T-cells on target cells. Namely, by multispecific binding of the antigen binding protein to CD3 and to a target cell, e.g. a tumor cell, cell lysis of the target cell may be induced. Antigen binding proteins with a CD3 binding site and their production are known in the art (and described for example in Kipriyanov et al., 1999, Journal of Molecular Biology 293:41-56, Le Gall et al., 2004, Protein Engineering, Design & Selection, 17/4:357-366).

Besides quadroma derived antibodies, a variety of formats of multispecific recombinant antibody fragments have been designed. A particular format of multivalent, and optionally multispecific antibody fragments are named "tandem diabodies" (TandAb®), since their design is based on intermolecular pairing of $V_H$ and $V_L$ variable domains of two different polypeptides as described for diabodies (Holliger et al., 1993, Proc. Natl. Acad. Sci. USA, 90:6444-6448). The described antibodies are bispecific for a tumor antigen and CD3. In contrast to bivalent scFv-scFv (scFv)$_2$ tandems the tandem diabodies are tetravalent, because they have four antigen-binding sites. The tandem diabodies are devoid of immunoglobulin constant domains. It was reported that the tandem diabodies have advantages such as a high affinity, a higher avidity, lower clearance rates and exhibit a favorable in vitro and in vivo efficiency (Kipriyanov et al. J. Mol. Biol. (1999) 293, 41-56 and Kipriyanov Meth. Mol. Biol. (2009) 562, 177-193).

Such bispecific tandem diabodies can make a bridge between a tumor cell (e.g. B-CLL cell) and a CD3$^+$ T cell of the human immune system, thus permitting killing of the tumour cell. The tight binding of the tumor cell and the T cell induces the destruction of the tumor cell. While such tandem diabodies have proved to be favorable for therapeutic applications, e.g. for therapeutic concepts for the treatment of tumors, there remains a need for improved antigen-binding molecules.

To facilitate toxicology assessment of T cell recruiting multispecific antibody fragments in non-human primates (NHP) during preclinical development, a cross-reactive CD3 binding domain is desirable.

The murine IgG clone SP34 (EMBO J. 1985. 4(2):337-344; J. Immunol. 1986, 137(4):1097-100; J. Exp. Med. 1991, 174:319-326; J. Immunol. 1991, 147(9):3047-52) binds to human and cynomolgus CD3E has been selected for humanization.

SUMMARY OF INVENTION

The present invention provides an antigen binding protein comprising at least one CD3 binding site, wherein the CD3 binding site comprises:
(a) a variable heavy chain domain (VH) selected from the VH as depicted in SEQ ID NO:6, 7, 8 or 9 and a variable light chain domain (VL) selected from the VL as depicted in SEQ ID NO:1, 2, 3 or 4; or
(b) a variable heavy chain domain (VH) having sequence identity of at least 95% compared to the VH as depicted in SEQ ID NO:8, wherein the variable residue at position 111 is Y or H and a variable light chain domain (VL) having sequence identity of at least 95% compared to the VL as in SEQ ID NO:3, wherein the amino acid residue at position 49 is G or A, or
c) a variable heavy chain domain (VH) incorporating 1 to 5 conserved amino acid substitutions compared to the VH as depicted in SEQ ID NO:8, wherein the amino acid residue at position 111 is Y or H, and a variable light chain domain (VL) incorporating 1 to 5 conserved amino acid substitutions compared to the VL as depicted in SEQ ID NO:3, wherein the amino acid residue at position 49 is G or A.

In certain embodiments the antigen binding protein comprising at least one CD3 binding site as defined above is not a bispecific binding protein that specifically binds to human CD33 and human CD3, wherein the CD3 binding site comprises at least one antibody variable heavy chain domain and at least one variable light chain domain forming an antigen binding site for human CD3 and the anti-CD3 variable light chain domain is selected from the group consisting of SEQ ID NOs:1-3 and the anti-CD3 variable heavy chain domain is selected from the group consisting of SEQ ID NOs:6-8. In particular embodiments the antigen binding protein is not a bispecific tandem diabodies that bind to CD33 and CD3, wherein the anti-CD3 variable light chain domain is selected from the group consisting of SEQ ID NOs:1-3 and the anti-CD3 variable heavy chain domain is selected from the group consisting of SEQ ID Nos:6-8. In further embodiments of the present invention the antigen binding protein comprising at least one CD3 binding site as defined above is not a bispecific binding protein that specifically binds to human CD33 and human CD3

DETAILED DESCRIPTION OF THE INVENTION

Definitions

Figure 1A:
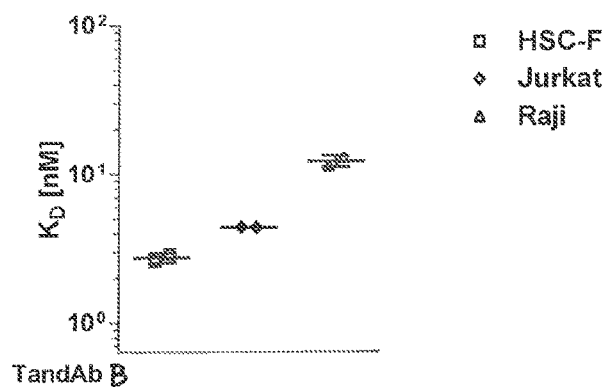
FIGS. 1A and 1B: Binding and cytotoxic activity of tandem diabodies containing different anti-CD3 domains. (A) Human CD19$^+$ Raji cells, human CD3$^+$ Jurkat cells and cynomolgus CD3$^+$ HSC-F cells were stained on ice with 10 µg/mL tandem diabody TandAb B, containing the CD3-binding domain var_w (SEQ ID NOs: 1 and 6) in combination with a CD19-binding domain. Cell-surface bound tandem diabody was detected by anti-His mAb followed by FITC-conjugated goat anti-mouse IgG. Mean fluorescence intensities determined by flow cytometry were modeled as sigmoidal dose-response by non-linear regression to calculate $K_D$. (B) $EC_{50}$ values were determined in cytotoxicity assays with calcein-labeled EGFRvIII+ F98 target cells and PBMC as effector cells at an E:T ratio of 50:1 with 4 h incubation time. The $EC_{50}$ was calculated by non-linear regression of the data modeled as a sigmoidal curve.

The term "antigen binding protein" refers to an immunoglobulin derivative with antigen binding properties, i.e. immunoglobulin polypeptides or fragments thereof that contain an antigen binding site. The binding protein comprises variable domains of an antibody or fragments thereof. Each antigen-binding site is formed by an antibody, i.e. immunoglobulin, variable heavy chain domain (VH) and an antibody variable light chain domain (VL) binding to the same epitope, whereas the variable heavy chain domain (VH) comprises three heavy chain complementarity determining regions (CDR): CDR1, CDR2 and CDR3; and the variable light chain domain (VL) comprises three light chain complementary determining regions (CDR): CDR1, CDR2 and CDR3. In some instances, the binding protein according to some embodiments herein is devoid of immunoglobulin constant domains. In some instances, the variable light and heavy chain domains forming the antigen binding site is covalently linked with one another, e.g. by a peptide linker, or in other instances, the variable light and heavy chain domains non-covalently associate with one another to form the antigen binding site. The term "antigen binding protein" refers also to monoclonal antibodies of the classes IgA, IgD, IgE, IgG or IgM and antibody fragments or antibody derivatives including, for example, Fab, Fab', F(ab')$_2$, Fv fragments, single-chain Fv, tandem single-chain Fv ((scFv)$_2$, diabody, flexibody (WO 03/025018) and tandem diabody (TandAb®)(Kipriyanov et al., 1999, J. Mol. Biol, 293:41-56; Cochlovius et al., 2000, Cancer Res., 60:4336-4341; Reusch et al., 2004, Int. J. Cancer, 112:509-518, Kipriyanov, 2009, Methods Mol Biol, 562:177-93; McAleese and Eser, 2012, Future Oncol. 8:687-95). "TandAb" is a trademark of Affimed used for designating a tandem diabody. In the context of the present invention "TandAb" and "tandem diabodies" are used as synonyms.

While humanization by grafting the murine VH CDRs onto the most homologous human VH framework (human VH3_72) resulted in a molecule retaining function, grafting the murine VL CDRs onto the human VL framework with highest homology (human vλ7_7a) resulted surprisingly in either poorly expressed tandem diabodies or tandem diabodies which failed to recognize CD3.

Therefore, it is the object of the present invention to provide CD3 binding domains with functional VL/VH pairing, good stability, good expression and other biophysical properties.

The inventors have discovered that functional VL/VH pairing can be achieved by another human VL framework. The inventors have discovered that the change from a murine VL framework of the λ chain to a human VL framework of the κ chain (human Vκ1_39) resulted in binding proteins showing superior CD3 binding affinity, expressability and cytotoxic potency in target cell lysis induced by bispecific tandem diabodies. But such molecules were weaker in stability and other biophysical properties. In a further step it has been found that the amino acids in positions VH111 and VL49 (which directly contact each other according to the model) are crucial for the binding and stability properties of this CD3 binding site, for example in a bispecific antibody molecule, in particular multimeric antigen binding proteins such as, for example, diabodies or tandem diabodies. The mutations of VH111 to Y or H as well as in addition the mutation of VL49 from G to A surprisingly creates binding domains with improved stability properties, while the original binding affinities and/or cytotoxicity are retained. An improved 7 day stability at 40° C. can be observed for these proteins, in particular when they are expressed as dimeric tandem diabodies. Further the clones demonstrate increased content of correctly dimerized tandem diabodies as well as improved recovery.

In certain embodiments the CD3 binding site comprises a VH, wherein the VH framework is derived from a human VH3_72 framework and a VL, wherein the VL framework is derived from human Vκ1_39. In a particular embodiment the CD3 binding site comprises a VH selected from the VH as depicted in SEQ ID NO:8 or 9 and a VL selected from the VL as depicted in SEQ ID NO:3 or 4. In certain instances the CD3 binding site comprises (i) a VH as depicted in SEQ ID NO:8 and a VL as depicted in SEQ ID NO:3 or (ii) a VH as depicted in SEQ ID NO:9 and a VL as depicted in SEQ ID NO:4, (iii) a VH as depicted in SEQ ID NO:7 and a VL as depicted in SEQ ID NO:2; or (iv) a VH as depicted in SEQ ID NO:6 and a VL as depicted in SEQ ID NO:1. In alternative embodiments, the heavy and light chain domains incorporate homologues or variants of the sequences described herein and binding specifically to CD3. Accordingly in some embodiments, a VL or VH sequence to CD3 is similar to, but not identical to, the amino acid sequence depicted in SEQ ID NO:3 or 8, wherein (i) the amino acid residue at position VH111 is F, Y or H or (ii) the amino acid residue at position VH111 is F, Y or H and the amino acid residue at position VL49 is G or A. In certain embodiments, a VH or VL variant sequence has a sequence identity of 99%, 98%, 97%, 96%, 95%, 94%, 93%, 92%, 91%, 90%, 89%, 88%, 87%, 86%, 85%, 84%, 83%, 82%, 81%, or 80% compared to the sequence as depicted in SEQ ID NO:3 or 8 and which binds specifically to CD3, wherein (i) the amino acid residue at position VH111 is F, Y or H or (ii) the amino acid residue at position VH111 is F, Y or H and the amino acid residue at position VL49 is G or A.

In further embodiments, a VH and/or VL variant incorporates 1, 2, 3, 4, 5, 6, 7 or 8 conserved amino acid substitutions. Conservative substitutions include, among the aliphatic amino acids interchange of alanine, valine, leucine, and isoleucine; interchange of the hydroxyl residues serine and threonine, exchange of the acidic residues aspartate and glutamate, substitution between the amide residues asparagine and glutamine, exchange of the basic residues lysine and arginine, and replacements among the aromatic residues phenylalanine and tyrosine. In certain instances a VH and/or VL variant incorporates such 1, 2, 3, 4, 5, 6, 7 or conserved amino acid substitutions under the proviso that (i) the amino acid residue at position VH111 is F, Y or H or (ii) the amino acid residue at position VH111 is F, Y or H and the amino acid residue at position VL49 is G or A. In certain instances such substitutions are not within the CDRs.

In yet further embodiments, a VH or VL variant incorporates substitutions that enhance properties of the CDR such as increase in stability, expression, recovery, binding affinity to CD3 and/or cytotoxic potency.

Furthermore, in certain embodiments, the antigen binding protein is multivalent, i.e. has two, three or more binding sites for CD3

In certain embodiments, the antigen binding protein according to the invention is multifunctional. The term multifunctional as used herein means that a binding protein of the invention exhibits two, three or more different biological functions, wherein one function is the binding to CD3. For example, the different biological functions are different specificities for different antigens. In certain instances, the multifunctional antigen binding protein is multispecific, i.e. has binding specificity to CD3 and one, two or more further antigens. Such multispecific antigen binding proteins include, for example, multispecific F(ab')$_2$, Fv fragments, single-chain Fv, tandem single-chain Fv ((scFv)$_2$), diabody, flexibody (WO 03/025018) and tandem diabody.

In certain embodiments, the antigen binding protein comprises at least one CD3 binding site and at least one further antigen-binding site specific for a bacterial substance, viral protein, autoimmune marker or an antigen present on a particular cell such as a cell surface protein of a B-cell, T-cell, natural killer (NK) cell, myeloid cell, phagocytic cell or tumor cell. Such antigen binding molecules are able to cross-link two cells and can be used to direct T cells to a specific target.

Examples of such targets may be tumor cells or infectious agents such as viral or bacterial pathogens, for example dengue virus, herpes simplex, influenza virus, HIV or cells carrying autoimmune targets such as IL-2, an autoimmune marker or an autoimmune antigen.

In certain embodiments the at least one further antigen-binding site is specific for an antigen of a tumor cell. Antigens for tumor cells may be tumor antigens and cell surface antigens on the respective tumor cell, for example specific tumor markers. Such multispecific antigen binding protein binds to both the tumor cell and the CD3 on T cells thereby triggering the cytotoxic response induced by the T cell. The term "tumor antigen" as used herein comprises tumor associated antigen (TAA) and tumor specific antigen (TSA). A "tumor associated antigen" (TAA) as used herein refers to a protein which is present on tumor cells, and on normal cells during fetal life (once-fetal antigens), and after birth in selected organs, but at much lower concentration than on tumor cells. A TAA may also be present in the stroma in the vicinity of the tumor cell but expressed at lower amounts in the stroma elsewhere in the body. In contrast, the term "tumor specific antigen" (TSA) refers to a protein expressed by tumor cells. The term "cell surface antigen" refers to any antigen or fragment thereof capable of being recognized by an antibody on the surface of a cell.

Examples of antigens of tumor cells include but are not limited to CD19, CD20, CD30, CD33, the laminin receptor precursor protein, EGFR1, EGFR2, EGFR3, EGFRvIII, Ep-CAM, PLAP, Thomsen-Friedenreich (TF) antigen, MUC-1 (mucin), IGFR, CD5, IL4-R alpha, IL13-R, FcERI and IgE as described in the art.

In another embodiments the antigen binding protein may comprise at least one CD3 binding site and at least one further antigen-binding site specific for a molecule selected from the group consisting of a drug, toxin, radionucleotide, enzyme, albumin, e.g. serum albumin, and lipoprotein, naturally occurring ligands such as cytokines or chemokines. If the target molecule is albumin, the albumin or serum albumin may be selected from the group of origins consisting of human, bovine, rabbit, canine and mouse.

In certain embodiments, the binding protein is multispecific with a first specificity to CD3 and a second specificity to CD19, CD30, CD33, EGFRvIII or HSA. In a particular embodiment the multispecific binding protein with a first specificity to CD3 does not have a second specificity to CD33.

In another aspect, an antigen binding protein according to the invention is a multimer, i.e. comprises two, three or more polypeptides forming at least one antigen binding site for CD3. As used herein, "multimer" refers to a complex of two or more polypeptides. In certain embodiments, the polypeptides of a multimer are non-covalently associated with each other, in particular with the proviso that there is no covalent bound between the polypeptides. In certain embodiments, the multimer is homomeric, i.e. comprises identical polypeptides. The term "polypeptide" refers to a polymer of amino acid residues linked by amide bonds. The polypeptide is, in certain embodiments, a single chain fusion protein, which is not branched. In the polypeptide the variable antibody domains are linked one after another. The polypeptide, in other embodiments, may have contiguous amino acid residues in addition to the variable domain N-terminal and/or C-terminal residues. For example, such contiguous amino acid residues may comprise a Tag sequence, in some embodiments at the C-terminus, which is contemplated to be useful for the purification and detection of the polypeptide.

In certain embodiments the multimer is dimeric, i.e. comprises two polypeptides. Examples of a multimer encompassed by the invention are diabody, tandem diabody and flexibody.

In certain embodiments the multimer is an antigen binding protein in the format of a tandem diabody. Such tandem diabodies are constructed by linking four antibody variable binding domains, for example two VH and two VL, in a single gene construct enabling non-covalent dimerization. In such tandem diabodies the linker length is such that it prevents intramolecular pairing of the variable domains so that the molecule cannot fold back upon itself to form a single-chain diabody, but rather is forced to pair with the complementary domains of another chain. The domains are also arranged such that the corresponding VH and VL domains pair during this dimerization. Following expression from gene construct, two polypeptide chains fold head-to-tail forming a functional non-covalent dimer of approximately 105 kDa (Kipriyanov Meth. Mol. Biol. (2009) 562, 177-193, McAleese and Eser, 2012, Future Oncol. 8:687-95). Despite the absence of intermolecular covalent bonds, the dimer is highly stable once formed, remains intact and does not revert back to the monomeric form.

Tandem diabodies have a number of properties that provide advantages over traditional monoclonal antibodies and other smaller Fv molecules. Tandem diabodies contain only antibody variable domains and therefore lack any of the side effects that may be associated with the Fc moiety. Because tandem diabodies are multivalent and allow for bivalent binding to CD3, the avidity is the same as that of an IgG. The size of a tandem diabody, at in certain embodiments approximately 105 kDa, is smaller than that of an IgG, which may allow for enhanced tumor penetration. However, this size is well above the renal threshold for first-pass clearance, offering a pharmacokinetic advantage compared with smaller antibody formats based on antibody-binding sites or non-antibody scaffolds. Tandem diabodies are well expressed in host cells, for example, mammalian CHO cells. It is contemplated that robust upstream and downstream manufacturing process is available for tandem diabodies (e.g. Kipriyanov, Meth. Mol. Biol. (2009) 562, 177-193).

In certain instances, the multispecific antigen binding protein, for example, tandem diabody, described herein is designed to allow specific targeting of tumor cells by recruiting cytotoxic T-cells. This improves ADCC (antibody dependent cell-mediated cytotoxicity) compared to conventional antibodies. Antibodies are not capable of directly recruiting cytotoxic T-cells. In contrast, by engaging CD3 molecules expressed specifically on these cells, the multispecific antigen binding protein, for example, the tandem diabody can crosslink a cytotoxic T-cell with a tumor cells in a highly specific fashion, thereby significantly increasing the cytotoxic potential of such molecules.

In one aspect, the multimer is a bispecific tandem diabody, wherein each polypeptide of the bispecific tandem diabody comprises four variable domains, a VL and a VH of the CD3 having a second specificity different from CD3. In certain embodiments, four variable domains are linked by peptide linkers L1, L2 and L3 and in some instances arranged from the N- to the C-terminus as follows:
(i) VL (CD3)-L1-VH (second antigen-binding site)-L2-VL (second antigen binding site)-L3-VH(CD3); or
(ii) VH (CD3)-L1-VL (second antigen-binding site)-L2-VH (second antigen-binding site)-L3-VL (CD3); or
(iii) VL (second antigen-binding site)-L1-VH(CD3)-L2-VL (CD3)-L3-VH (second antigen-binding site); or
(iv) VH (second antigen-binding site)-L1-VL (CD3)-L2-VH (CD3)-L3-VL (second antigen-binding site).

In certain embodiments, the "another antigen-binding site" is specific for a tumor antigen, for example CD19, CD30, CD33 or EGFRvIII. In a particular embodiment the tumor antigen is not CD33.

The length of the linkers influences the flexibility of the tandem diabody. Accordingly, in some embodiments, the length of the peptide linkers L1, L2 and L3 is such that the domains of one polypeptide can associate intermolecularly with the domains of another polypeptide to form the dimeric antigen-binding tandem diabody. In certain embodiments, such linkers are "short", i.e. consist of 0, 1, 2, 3, 4, 5, 6, 7, 8, 9, 10, 11 or 12 amino acid residues. Thus, in certain instances, the linkers consist of about 12 or less amino acid residues. In the case of 0 amino acid residues the linker is a peptide bond. Such short linkers favor the intermolecular dimerization of the two polypeptides by binding and forming correct antigen-binding sites between antibody variable light chain domains and antibody variable heavy chain domains of different polypeptides. Shortening the linker to about 12 or less amino acid residues generally prevents adjacent domains of the same polypeptide chain from intramolecular interaction with each other. In some embodiments, these linkers consist of about 3 to about 12, in particular about 3 to about 10, for example 4, 5, 6, 7, 8 or 9 contiguous amino acid residues.

Regarding the amino acid composition of the linkers, peptides are selected that do not interfere with the dimerization of the two polypeptides. For example, linkers comprising glycine and serine residues generally provide protease resistance. The amino acid sequence of the linkers can be optimized, for example, by phage-display methods to improve the antigen binding and production yield of the antigen-binding polypeptide dimer. Examples of peptide linkers suitable for a tandem diabody according to the invention are GGSGGS (SEQ ID NO:16), GGSG (SEQ ID NO:17), or GGSGG (SEQ ID NO:18).

The multimeric antigen binding protein described herein is produced, in some embodiments, by expressing polynucleotides encoding the polypeptide of the tandem diabody which associates with another identical polypeptide to form the antigen-binding tandem diabody. Therefore, another aspect is a polynucleotide, e.g. DNA or RNA, encoding the polypeptide of a multimeric antigen binding protein described herein, for example a tandem diabody.

The polynucleotide is constructed by known methods such as by combining the genes encoding the antibody variable domains either separated by peptide linkers or, in other embodiments, directly linked by a peptide bond, into a single genetic construct operably linked to a suitable promoter, and optionally a suitable transcription terminator, and expressing it in bacteria or other appropriate expression system such as, for example CHO cells. Depending on the vector system and host utilized, any number of suitable transcription and translation elements, including constitutive and inducible promoters, may be used. The promoter is selected such that it drives the expression of the polynucleotide in the respective host cell.

In some embodiments, the polynucleotide is inserted into a vector, preferably an expression vector, which represents a further embodiment of the invention. This recombinant vector can be constructed according to known methods.

A variety of expression vector/host systems may be utilized to contain and express the polynucleotide encoding the polypeptide, for example, of the described tandem diabody. Examples of expression vectors for expression in *E. coli* are pSKK (Le Gall et al., J Immunol Methods. (2004) 285(1):111-27) or pcDNA5 (Invitrogen) for expression in mammalian cells.

Thus, the antigen-binding tandem diabody as described herein, in some embodiments, is produced by introducing a vector encoding the polypeptide as described above into a host cell and culturing said host cell under conditions whereby the polypeptide chains are expressed, may be isolated and, optionally, further purified. For the isolation and purification of the polypeptides no Taq's are necessary, which is an advantage for in vivo administration.

In other aspects, provided herein are pharmaceutical compositions comprising the antigen binding protein according to the invention, for example a tandem diabody, a vector comprising the polynucleotide encoding the polypeptide of the antigen binding protein or a host cell transformed by this vector and at least one pharmaceutically acceptable carrier. The term "pharmaceutically acceptable carrier" includes, but is not limited to, any carrier that does not interfere with the effectiveness of the biological activity of the ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents. Prevention of the action of microorganisms may be ensured by the inclusion of various antibacterial and antifungal agents. Administration of the suitable compositions may be effected by different ways, e.g. by intravenous, intraperetoneal, subcutaneous, intramuscular, topical or intradermal administration. The route of administration, of course, depends on the kind of therapy and the kind of compound contained in the pharmaceutical composition. The dosage regimen will be determined by the attending physician and other clinical factors. As is well known in the medical arts, dosages for any one patient depends on many factors, including the patient's size, body surface area, age, sex, the particular compound to be administered, time and route of administration, the kind of therapy, general health and other drugs being administered concurrently.

The invention further provides a medical use or a method wherein the antigen binding protein as described herein above is administered in an effective dose to a subject, e.g., patient, for immunosuppressive treatment, e.g. in transplantation, the treatment of autoimmune disease, inflammatory disease, infectious disease, allergy or cancer (e.g. non-Hodgkin's lymphoma; chronic lymphocytic leukemia; Hodgkin's lymphoma; solid tumors e.g. those occurring in breast cancer, ovarian cancer, colon cancer, cancer of the kidney, or cancer of the bile duct; minimal residual disease; metastatic tumors e.g. those metastasizing in the lungs, bones, liver or brain). The antigen binding protein can be used in prophylactic or therapeutic settings, alone or in combination with current therapies.

The cancers that can be treated using the multispecific antigen binding protein of the present invention include but are not limited to primary and metastatic adrenal cortical cancer, anal cancer, aplastic anemia, bile duct cancer, bladder cancer, bone cancer, bone metastasis, CNS tumors, peripheral CNS cancer, breast cancer, Castleman's Disease, cervical cancer, childhood Non-Hodgkin's lymphoma, colon and rectum cancer, endometrial cancer, esophagus cancer, Ewing's family of tumors (e.g. Ewing's sarcoma), eye cancer, gallbladder cancer, gastrointestinal carcinoid tumors, gastrointestinal stromal tumors, gestational trophoblastic disease, hairy cell leukemia, Hodgkin's disease, Kaposi's sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma (adult soft tissue cancer), melanoma skin cancer, non-melanoma skin cancer, stomach cancer, testicular cancer, *thymus* cancer, thyroid cancer, uterine cancer (e.g. uterine sarcoma), vaginal cancer, vulvar cancer, and Waldenstrom's macro globulinemia.

An "effective dose" refers to amounts of the active ingredient that are sufficient to affect the course and the severity of the disease, leading to the reduction or remission of such pathology. An "effective dose" useful for treating and/or preventing these diseases or disorders may be determined using methods known to a skilled person (see for example, Fingl et al., The Pharmacological Basis of Therapeutics, Goodman and Gilman, eds. Macmillan Publishing Co., New York, pp. 1-46 (1975)).

In another aspect of the invention the antigen binding protein as described herein above is used in the manufacture of a immunosuppressive medicament or medicament for the treatment of autoimmune disease, inflammatory disease, infectious disease, allergy or cancer (e.g. non-Hodgkin's lymphoma; chronic lymphocytic leukaemia; Hodgkin's lymphoma; solid tumours e.g. those occurring in breast cancer, ovarian cancer, colon cancer, cancer of the kidney, or cancer of the bile duct; minimal residual disease; metastatic tumours e.g. those metastasizing the lungs, bones, liver or brain). Where specified, multispecific binding proteins have been described above as having a particular utility in the treatment of a specified disease, these antigen binding proteins may also be used in the manufacture of a medicament for that specified disease.

The methods for preparing pharmaceutical compositions, i.e. medicaments, and the clinical application of antigen binding proteins in the prevention and/or treatment of diseases such as, for example, cancer are known to the skilled artisan.

In a particular aspect of the invention the antigen binding protein is multispecifc and used for cancer therapy, because such multispecific antigen binding protein can be used to retarget cytotoxic effector cells against tumor cells. This therapeutic concept is well known in the art. For example, clinical studies showed tumor regression in patients treated with an anti-CD3 x antitumor bispecific antibody (e.g. Canevari, S. et al., J. Natl. Cancer Inst., 87:1463-1469, 1996) or patients treated with an anti-CD16 x antitumor bispecific antibody (e.g. Hartmann et al.; Clin Cancer Res. 2001; 7(7):1873-81). Proof-of-concept has also been shown for various recombinant bispecific antibody molecules comprising only variable domains (Fv) (Cochlovius et al.; Cancer Research, 2000, 60:4336-4341) or recently in clinical studies with monomeric single-chain Fv antibody molecules of the BiTE®-format (two single-chain antibodies of different specificities linked together; Amgen Germany; Bargou R. et al., Science, 2008, 321(5891):974-977; Baeuerle P A and Reinhardt C., Cancer Res. 2009, 69(12):4941-4944). The dimeric antigen binding proteins described herein can be used as medicaments and applied in methods of treatment in a similar way as the bispecific antibodies of the art, as they are capable of redirecting therapeutic, e.g. cytotoxic, mechanisms using the same combined antibody specificities. Further, immunosuppressive antibodies monospecific for CD3 such as Muromonab-CD3 are known for the treatment of transplant rejection, acute rejection of renal transplants (allografts), hepatic and cardiac transplants. Thus, antigen binding proteins specific for albumin and CD3 may be used in the same methods of treatments as the known monospecific anti-CD3 antibodies.

The antigen binding protein and the compositions thereof can be in the form of an oral, intravenous, intraperitoneal, or other pharmaceutically acceptable dosage form. In some embodiments, the composition is administered orally and the dosage form is a tablet, capsule, caplet or other orally available form. In some embodiments, the composition is parenteral, e.g. intravenous, intraperitoneal, intramuscular, or subcutaneous, and is administered by means of a solution containing the antigen-binding molecule.

A skilled person will readily be able without undue burden to construct and obtain the antigen binding proteins described herein by utilizing established techniques and standard methods known in the art, see for example Sambrook, Molecular Cloning A Laboratory Manual, Cold Spring Harbor Laboratory (1989) N.Y.; The Protein Protocols Handbook, edited by John M. Walker, Humana Press Inc. (2002); or Antibody engineering: methods and protocols/edited by Benny K. C. Lo; Benny K. C. II Series: Methods in molecular biology (Totowa, N.J.)).

Example 1

Generation of particular VL and VH comprised by the CD3 binding site of the antigen binding protein. In the first step, the murine VH CDRs of SP34 (BD Bioscience; J. Immunol. Methods., 1994, 178:195) were grafted onto the most homologous human framework (human VH3_72) of IgG1 yielding a chimeric binding domain composed of the newly humanized VH and the parental murine VL λ chain. Binding data showed that the chimeric molecule retained function. Thus, the humanized VH chain was not altered during the subsequent humanization steps for the VL chain.

For the humanization of the murine SP34 VL sequence, murine CDRs were grafted onto the human VL framework with highest homology to the parental murine framework (human Vλ7_7a). Constructs containing this closely related λ chain were generated by introducing back-mutations and assayed in the tandem diabody format in combination with a CD19 binding domain. The back-mutations were selected based on comparison of models of the original murine SP34 and the humanized variants containing the Vλ7_7a framework; they were selected to reduce steric clashes and preserve donor murine antibody CDR conformations when grafted onto the acceptor human framework. However, all of these λ chain-containing tandem diabodies were either poorly expressed or failed to recognize the antigen.

Therefore, an alternative method was chosen for humanizing the VL chain. In this second strategy, data of heavy and light chains was analyzed regarding optimal pairing of heavy and light chains. The grafting of the murine CDRs onto a fixed human framework (human Vκ1_39) was pursued. Thus, the λ chain was replaced by a κ chain. It was found that a Vκ1_39 framework for the light chain may be compatible with the VH3_72 framework that was used for humanization of the heavy chain (described above). Thereafter, it was tested whether the use of the Vκ1_39 framework in combination with the VH3_72 framework results in an Fv with improved VL/VH pairing, and could yield a humanized domain with good stability, expression, and other biophysical properties.

Several tandem diabodies were generated containing either a small set of individual mutations or combinations thereof. The back-mutations were selected to reduce steric clashes and preserve donor murine antibody CDR configurations when grafted onto the acceptor human framework. Most surprisingly, the κ chain-containing antigen binding proteins demonstrated superior properties with acceptable expression and binding to human and cynomolgus CD3. Based on their biophysical and functional properties, as well as their respective expression yields, the Vκ binding domains var_w was identified as the most promising candidate, and hence was selected for further development. The initial stability of var_w could be significantly improved by following mutations in VL: D72→T72, K73→D73 and A74→F74 which resulted in candidate var_x.

Figure 1B:
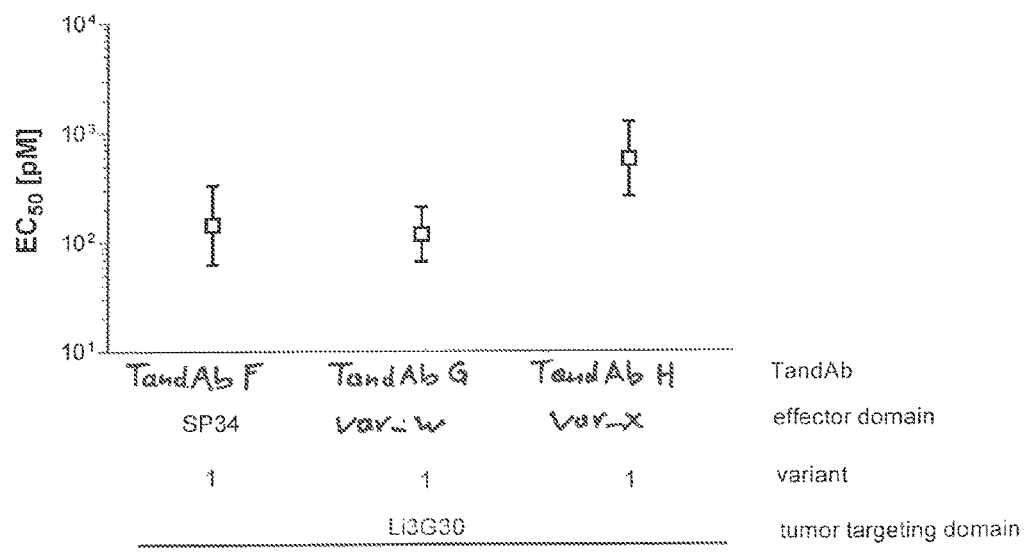

During the successive steps of humanizing the CD3 binding domain, var_w and var_x were combined with further antigen-binding sites other than anti-CD19, namely anti-EGFRvIII, anti-EpCAM and anti-CD30, to assay the ability of these two variants to pair with various antitumor antigen sites. Combination of var_w and var_x with these tumor target-binding sites yielded well-expressing and stable tandem diabodies that exhibited both target-binding and T cell-mediated cytotoxicity. FIG. 1A illustrates the binding activity of TandAb B, an antibody containing the CD3-binding domains var_w in combination with a CD19-binding domain, measured by flow cytometry. Binding affinities ($K_D$) of TandAb B to the CD19-expressing human cell line Raji, a $CD3^+$ human T cell line (Jurkat) and a cynomolgus CD3-expressing cell line (HSC-F) are shown. Cross-reactivity was observed without substantial differences in binding ($K_D$) to cynomolgus and human CD3. In FIG. 1B, a cytotoxicity assay is presented, in which tandem diabodies contain the CD3-binding domains var_w or var_x in combination with an EGFRvIII binding domain. The EGFRvIII-expressing cell line F98 was efficiently lysed in a 4 h cytotoxicity assay (calcein labeling) using human PBMC as effector cells. Tandem diabody-mediated target cell lysis by the var_w-containing TandAb G (SEQ ID NO:14) was comparable to that of a control TandAb F (SEQ ID NO:13) containing the parental murine CD3-binding domain of SP34.

Sequence and modeling analysis of clones var_w and var_x discovered a crucial role for amino acids in positions VH111 and VL49 (which directly contact each other according to the model) for the binding and stability properties of these variants in tandem diabodies. Several distinct mutations were introduced at these positions, and assayed individually or in tandem diabodies in combination with an EGFRvIII-binding domain. On position VH111 the mutations were from W to T, Q, N, S, F, Y, R or H; on position VL49 the mutations were from G to A, V, S, T or N. All resulting tandem diabodies were assayed for their binding properties, cytotoxicity, and stability.

Figure 2A:
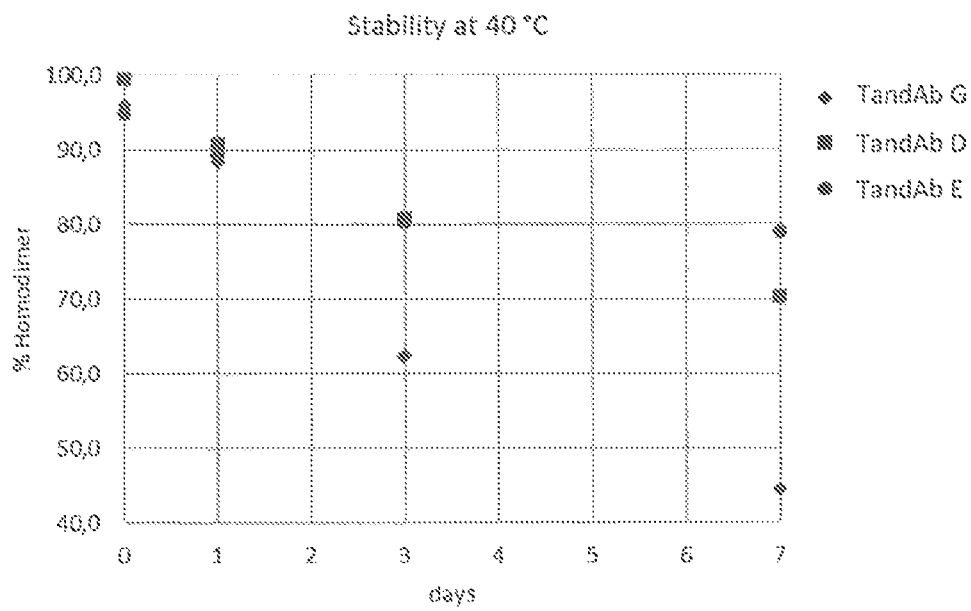
FIGS. 2A and 2B: Biophysical stability assayed via size-exclusion HPLC. TandAb G (SEQ ID NO:14), TandAb D (SEQ ID NO:11), and TandAb E (SEQ ID NO:12) were incubated at 40° C. for up to seven (7) days. (A) homodimer tandem diabody content, (B) % recovery
Figure 2B:
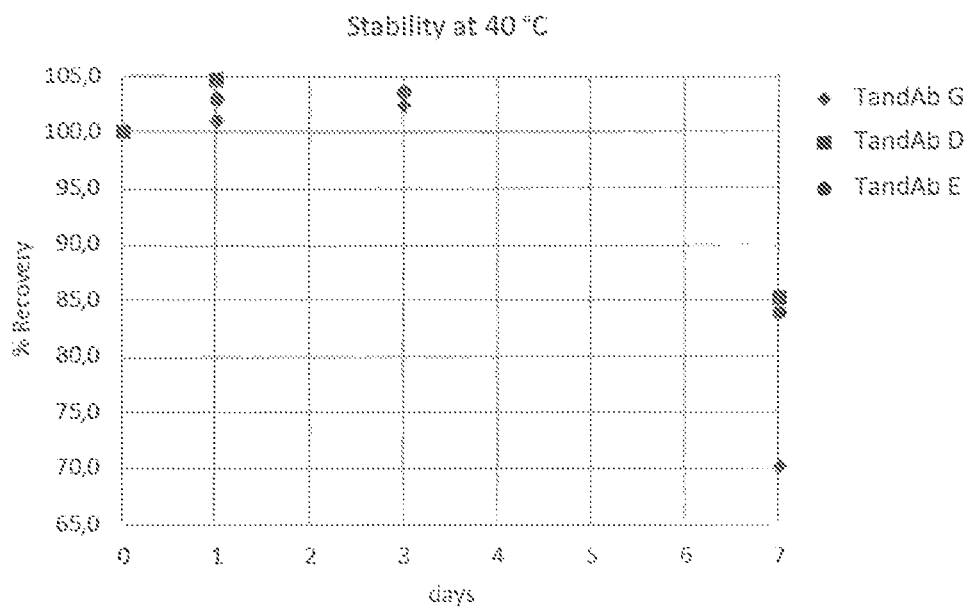

Mutation of VH111 from W to Y and VL49 from G to A created the CD3 binding domain var_y, while a single mutation of VH111 from W to H yielded the domain var_z; these binding domains produced the tandem diabodies TandAb D (var_y) (SEQ ID NO:11) and TandAb E (var_z) (SEQ ID NO:12), which exhibited improved stability properties relative to the parental var_w. VH111 occupies a special position in CDRH3 that, according to Shirai's rule (Kuroda et al, 2008, Proteins, 73:608), determines whether the conformation adopted by CDRH3 is extended or kinked. It resulted from the experiments that permissible substitutions for the W at this position must contain large aromatic rings such as F, Y, or H; otherwise a loss of binding is anticipated. Further, the modeled direct contact of VL49 with the backbone in the vicinity of VH111 also poses significant constraints on the nature of allowable residues. Using size-exclusion chromatography (SEC) to monitor the homodimer tandem diabody content, an improved 7 day stability at 40° C. was observed for these proteins. Both clones demonstrated increased desired tandem diabody homodimer content, relative to TandAb G (SEQ ID NO:14) containing the parental var_w, as well as improved recovery. FIGS. 2A and 2B depict the stability of TandAb D (SEQ ID NO:11), TandAb E (SEQ ID NO:12), and TandAb G (SEQ ID NO:14) over 7 days at 40° C.

Figure 3A:
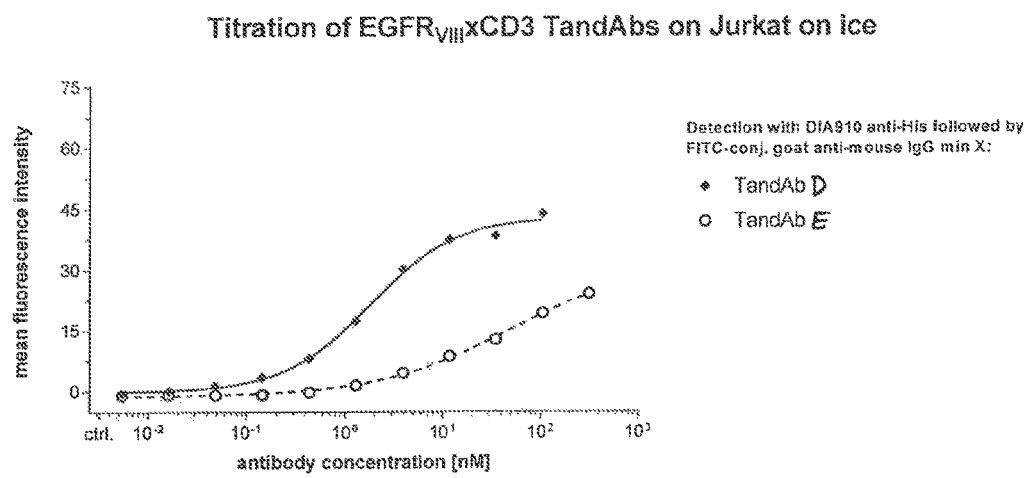
FIGS. 3A and 3B: Binding affinity and cross-reactivity of EGFRvIII/CD3 tandem diabodies with humanized anti-CD3 domains. Human CD3+ Jurkat cells (A) and cynomolgus CD3+ HSC-F cells (B) were stained with increasing concentrations of TandAb D (SEQ ID NO:11) ($K_D$ on Jurkat=1,822 nM, $K_D$ on HSC-F=3.4 nM) and TandAb E (SEQ ID NO:12) ($K_D$ on Jurkat=27.74 nM, $K_D$ on HSC-F=24.3 nM). Cell-surface bound tandem diabody was detected by anti-His mAb followed by FITC-conjugated goat anti-mouse IgG. To calculate $K_D$, mean fluorescence intensities determined by flow cytometry were modeled as sigmoidal dose-response by non-linear regression.
Figure 3B:
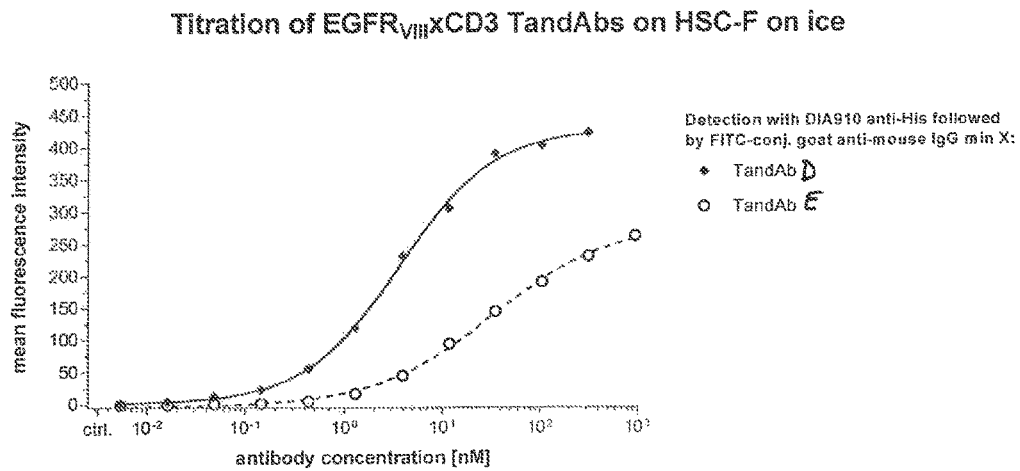

Surprisingly, functional assays further demonstrated that binding activity and cytotoxicity of these tandem diabodies was retained. FIGS. 3A and 3B present binding of titrated tandem diabodies TandAb D, containing var_y, and TandAb E (SEQ ID NO:12), containing var_z, to a CD3+ human T cell line (Jurkat) and a CD3+ cynomolgus cell line (HSC-F), as determined by flow cytometric analysis. $K_D$ values were calculated by non-linear regression, and are summarized in the tables below. Comparable binding affinities were observed for human and cynomolgus CD3, indicating cross-reactivity of the CD3-binding domain. TandAb D (SEQ ID NO:11) demonstrated >10 fold higher affinity to human CD3 ($K_D$=1.8 nM) than to TandAb E ($K_D$=27.7 nM) (SEQ ID NO:12).

Figure 4:
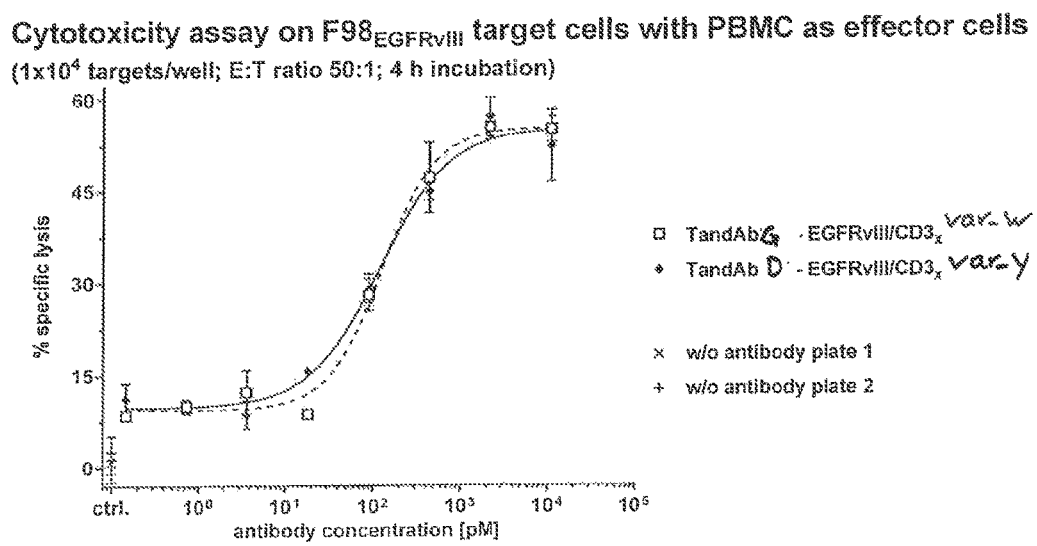
FIG. 4: Cytotoxic activity of EGFRvIII/CD3 tandem diabodies with humanized anti-CD3 domains. $EC_{50}$ values were determined in 4 h cytotoxicity assays with calcein-labelled EGFRvIII+ employing F98 as target cells and PBMC as effector cells at an E:T ratio of 50:1. $EC_{50}$ values were calculated by non-linear regression of the data modeled as a sigmoidal curve

TandAb D (SEQ ID NO:11), containing var_y, and its predecessor TandAb G (SEQ ID NO:14), containing var_w, were directly compared in a 4 h calcein release cytotoxicity assay with the EGFRvIII-expressing cell line F98, used as target cells, and human PBMC, used as effector cells. Target cell lysis induced by both antibodies was observed in a concentration-dependent manner, and exhibited comparable potency (TandAb G $EC_{50}$=129 pM, TandAb D $EC_{50}$=122 pM). Titration curves are shown in FIG. 4.

In summary, starting from the murine clone SP34, the VH and VL chains were subjected to a stepwise humanization by CDR-grafting. Stability of the humanized molecules was further increased in tandem diabodies by point mutations of framework residues, and selection of those substitutions that preserved the binding activity and cytotoxicity. The two optimized CD3 binding domains, var_y and var_z, demonstrated very good cross-reactivity to cynomolgus CD3. Target affinities of the optimized domains differed by approximately 10-fold, enabling the generation of tandem diabodies with different affinities for T cell recruitment. The aligned VH and VL amino acid sequences of the CD3-binding domains (var_y and var_z), the two intermediates (var_w and var_x), and the parental murine clone (SP34) are presented in Table 1.

TABLE 1

Alignment of amino acid sequences of the VH and VL chains of the relevant clones generated in the course of humanization/optimization. Differences in the humanized VH chain relative to the parental murine sequence are highlighted in cursive and underlined. Back mutations in the VL from the human germline sequences to the murine sequence are highlighted in cursive and underlined. CDRs are in bold and underlined."

| SP34 humanized variant | Sequence Identifier | |
|---|---|---|
| | | light chain sequence |
| var_w | SEQ ID NO: 1 | DIQMTQSPSSLSASVGDRVTITCRSSTGAVTTSNYANW*V*QQK PGKAPK*G*LIGGTNKRAPGVPSRFSGS*LIGDK*ATLTISSLQPE DFATYYCALWYSNLWVFGQGTKVEIK |
| Var_x | SEQ ID NO: 2 | DIQMTQSPSSLSASVGDRVTITCRSSTGAVTTSNYANW*V*QQK PGKAPK*G*LIGGTNKRAPGVP*A*RFSGSGSGTDFTLTISSLQPE DFATYYCALWYSNLWVFGQGTKVEIK |
| Var_y | SEQ ID NO: 3 | DIQMTQSPSSLSASVGDRVTITCRSSTGAVTTSNYANW*V*QQK PGKAPKALIGGTNKRAPGVPSRFSGS*LIGDK*ATLTISSLQPE DFATYYCALWYSNLWVFGQGTKVEIK |
| Var_z | SEQ ID NO: 4 | DIQMTQSPSSLSASVGDRVTITCRSSTGAVTTSNYANW*V*QQK PGKAPK*G*LIGGTNKRAPGVPSRFSGS*LIGDK*ATLTISSLQPE DFATYYCALWYSNLWVFGQGTKVEIK |
| murine SP34 | SEQ ID NO: 5 | QAVVTQESALTTSPGETVTLTCRSSTGAVTTSNYANWVQEKP DHLFTGLIGGTNKRAPGVPARFSGSLIGDKAALTITGAQTED EAIYFCALWYSNLWVFGGGTKLTVL |
| | | heavy chain sequence |
| var_w | SEQ ID NO: 6 | EVQLVESGGGLVQP*G*GSL*R*LSCAASGFTF*STYAMN*WVRQAPGKGLEWV*GR* IRSKYNNYATYYADSVKDRFTISRDDS*KNS*LYLQMN*S*LKTEDTA*VY*YCAR HGNFGNSYVSWFAYWGQGTLVTVSS |
| Var_x | SEQ ID NO: 7 | EVQLVESGGGLVQP*G*GSL*R*LSCAASGFTF*STYAMN*WVRQAPGKGLEWV*GR* IRSKYNNYATYYADSVKDRFTISRDDS*KNS*LYLQMN*S*LKTEDTA*VY*YCAR HGNFGNSYVSWFAYWGQGTLVTVSS |
| Var_y | SEQ ID NO: 8 | EVQLVESGGGLVQP*G*GSL*R*LSCAASGFTF*STYAMN*WVRQAPGKGLEWV*GR* IRSKYNNYATYYADSVKDRFTISRDDS*KNS*LYLQMN*S*LKTEDTA*VY*YCAR **HGNFGNSYVS*Y*FAY**WGQGTLVTVSS |
| Var_z | SEQ ID NO: 9 | EVQLVESGGGLVQP*G*GSL*R*LSCAASGFTF*STYAMN*WVRQAPGKGLEWV*GR* IRSKYNNYATYYADSVKDRFTISRDDS*KNS*LYLQMN*S*LKTEDTA*VY*YCAR **HGNFGNSYVS*H*FAY**WGQGTLVTVSS |
| Murine SP34 | SEQ ID NO: 10 | EVQLVESGGGLVQPKGSLKLSCAASGFTF*NTYAMN*WVRQAPGKGLEWVA*R* IRSKYNNYATYYADSVKDRFTISRDDSQSILYLQMNNLKTEDTAMYYCVR HGNFGNSYVSWFAYWGQGTLVTVSS |

What is claimed is:

1. An antigen binding protein comprising at least one CD3 binding site, wherein the CD3 binding site comprises:
   (a) a variable heavy chain domain (VH) as depicted in SEQ ID NO:8 and a variable light chain domain (VL) as depicted in SEQ ID NO:3; or
   (b) a variable heavy chain domain (VH) as depicted in SEQ ID NO:9 and a variable light chain domain (VL) as depicted in SEQ ID NO:4; or
   (c) a variable heavy chain domain (VH) as depicted in SEQ ID NO:7 and a variable light chain domain (VL) as depicted in SEQ ID NO:2; or
   (d) a variable heavy chain domain (VH) as depicted in SEQ ID NO:6 and a variable light chain domain (VL) as depicted in SEQ ID NO:1.

2. The antigen binding protein according to claim 1, wherein the protein comprises at least one further functional domain.

3. The antigen binding protein according to claim 2, wherein the at least one further functional domain is a further antigen binding site.

4. The antigen binding protein according to claim 3, wherein the further antigen binding site is specific for a tumor cell.

5. The antigen binding protein according to claim 1, wherein the antigen binding protein is multivalent.

6. The antigen binding protein according to claim 5, wherein the antigen binding protein is multispecific.

7. The antigen binding protein according to claim 6, wherein the antigen binding protein is multimeric.

8. The antigen binding protein according to claim 6, wherein the antigen binding protein is dimeric, comprising a first polypeptide and a second polypeptide, each polypeptide having at least four variable chain domains linked one after another, wherein the antigen binding protein comprises at least one CD3 binding site according to claim 1 and at least one further antigen binding site specific to a second antigen.

9. The antigen binding protein according to claim 8, wherein each polypeptides has at least four variable domains fused with one another by peptide linkers L1, L2 and L3 in the order of:
   (i) VL (CD3)-L1-VH (2nd antigen)-L2-VL (2nd antigen)-L3-VH(CD3);
   (ii) VH (CD3)-L1-VL (2nd antigen)-L2-VH (2nd antigen)-L3-VL (CD3);
   (iii) VL (2nd antigen)-L1-VH(CD3)-L2-VL (CD3)-L3-VH (2nd antigen); or
   (iv) VH (2nd antigen)-L1-VL (CD3)-L2-VH(CD3)-L3-VL (2nd antigen).

10. The antigen binding protein according to claim 9, wherein linkers L1, L2 and L3 consist of about 12 or less amino acid residues.

11. A pharmaceutical composition comprising (i) the antigen binding protein according to claim 1, and (ii) a pharmaceutically acceptable carrier.

* * * * *

UNITED STATES PATENT AND TRADEMARK OFFICE
CERTIFICATE OF CORRECTION

PATENT NO. : 10,066,015 B2
APPLICATION NO. : 14/820462
DATED : September 4, 2018
INVENTOR(S) : Eugene Zhukovsky et al.

Page 1 of 1

It is certified that error appears in the above-identified patent and that said Letters Patent is hereby corrected as shown below:

On the Title Page

Item [73]:
"Affirmed GmbH"
Should read:
--Affimed GmbH--

Signed and Sealed this
Fourth Day of December, 2018

Andrei Iancu
*Director of the United States Patent and Trademark Office*

SEQUENCE LISTING

<160> NUMBER OF SEQ ID NOS: 18

<210> SEQ ID NO 1
<211> LENGTH: 110
<212> TYPE: PRT
<213> ORGANISM: Artificial Sequence
<220> FEATURE:
<221> NAME/KEY: SOURCE
<222> LOCATION: 1..110
<223> OTHER INFORMATION: /mol_type="protein"
      /note="VL of var_w"
      /organism="Artificial Sequence"

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Gly Leu Ile Gly Gly Thr Asn Lys Arg Ala Pro Gly Val Pro Ser Arg
    50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys
            100                 105                 110

<210> SEQ ID NO 2
<211> LENGTH: 110
<212> TYPE: PRT
<213> ORGANISM: Artificial Sequence
<220> FEATURE:
<221> NAME/KEY: SOURCE
<222> LOCATION: 1..110
<223> OTHER INFORMATION: /mol_type="protein"
      /note="VL of var_x"
      /organism="Artificial Sequence"

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Gly Leu Ile Gly Gly Thr Asn Lys Arg Ala Pro Gly Val Pro Ala Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys
            100                 105                 110

<210> SEQ ID NO 3
<211> LENGTH: 110
<212> TYPE: PRT
<213> ORGANISM: Artificial Sequence
<220> FEATURE:
<221> NAME/KEY: SOURCE
<222> LOCATION: 1..110
<223> OTHER INFORMATION: /mol_type="protein"
      /note="VL of var_y"
      /organism="Artificial Sequence"

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Ala Leu Ile Gly Gly Thr Asn Lys Arg Ala Pro Gly Val Pro Ser Arg
    50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys
            100                 105                 110

<210> SEQ ID NO 4
<211> LENGTH: 110
<212> TYPE: PRT
<213> ORGANISM: Artificial Sequence
<220> FEATURE:
<221> NAME/KEY: SOURCE
<222> LOCATION: 1..110
<223> OTHER INFORMATION: /mol_type="protein"
      /note="VL of var_z"
      /organism="Artificial Sequence"

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Gly Leu Ile Gly Gly Thr Asn Lys Arg Ala Pro Gly Val Pro Ser Arg
    50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys
            100                 105                 110

<210> SEQ ID NO 5
<211> LENGTH: 109
<212> TYPE: PRT
<213> ORGANISM: Artificial Sequence
<220> FEATURE:
<221> NAME/KEY: SOURCE
<222> LOCATION: 1..109
<223> OTHER INFORMATION: /mol_type="protein"
      /note="VL of murine SP34"
      /organism="Artificial Sequence"

<400> SEQUENCE: 5

Gln Ala Val Val Thr Gln Glu Ser Ala Leu Thr Thr Ser Pro Gly Glu
1               5                   10                  15

```
Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
            35                  40                  45

Leu Ile Gly Gly Thr Asn Lys Arg Ala Pro Gly Val Pro Ala Arg Phe
50                      55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
                100                 105
```

<210> SEQ ID NO 6
<211> LENGTH: 125
<212> TYPE: PRT
<213> ORGANISM: Artificial Sequence
<220> FEATURE:
<221> NAME/KEY: SOURCE
<222> LOCATION: 1..125
<223> OTHER INFORMATION: /mol_type="protein"
      /note="VH of var_w"
      /organism="Artificial Sequence"

<400> SEQUENCE: 6

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
                100                 105                 110

Ala Tyr Trp Gly Gln Gly Thr Leu Val Thr Val Ser Ser
            115                 120                 125
```

<210> SEQ ID NO 7
<211> LENGTH: 125
<212> TYPE: PRT
<213> ORGANISM: Artificial Sequence
<220> FEATURE:
<221> NAME/KEY: SOURCE
<222> LOCATION: 1..125
<223> OTHER INFORMATION: /mol_type="protein"
      /note="VH of var_x"
      /organism="Artificial Sequence"

<400> SEQUENCE: 7

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
            35                  40                  45
```

Gly Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
                100                 105                 110

Ala Tyr Trp Gly Gln Gly Thr Leu Val Thr Val Ser Ser
        115                 120                 125

```
<210> SEQ ID NO 8
<211> LENGTH: 125
<212> TYPE: PRT
<213> ORGANISM: Artificial Sequence
<220> FEATURE:
<221> NAME/KEY: SOURCE
<222> LOCATION: 1..125
<223> OTHER INFORMATION: /mol_type="protein"
      /note="VH of var_y"
      /organism="Artificial Sequence"

<400> SEQUENCE: 8
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Tyr Phe
                100                 105                 110

Ala Tyr Trp Gly Gln Gly Thr Leu Val Thr Val Ser Ser
        115                 120                 125

```
<210> SEQ ID NO 9
<211> LENGTH: 125
<212> TYPE: PRT
<213> ORGANISM: Artificial Sequence
<220> FEATURE:
<221> NAME/KEY: SOURCE
<222> LOCATION: 1..125
<223> OTHER INFORMATION: /mol_type="protein"
      /note="VH of var_z"
      /organism="Artificial Sequence"

<400> SEQUENCE: 9
```

Glu Val Gln Leu Val Glu Ser Gly Gly Gly Leu Val Gln Pro Gly Gly
1               5                   10                  15

Ser Leu Arg Leu Ser Cys Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
            85                  90                  95

Tyr Cys Ala Arg His Gly Asn Phe Gly Asn Ser Tyr Val Ser His Phe
            100                 105                 110

Ala Tyr Trp Gly Gln Gly Thr Leu Val Thr Val Ser Ser
        115                 120                 125

<210> SEQ ID NO 10
<211> LENGTH: 125
<212> TYPE: PRT
<213> ORGANISM: Artificial Sequence
<220> FEATURE:
<221> NAME/KEY: SOURCE
<222> LOCATION: 1..125
<223> OTHER INFORMATION: /mol_type="protein"
      /note="VH of murine SP34"
      /organism="Artificial Sequence"

<400> SEQUENCE: 10

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
            85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 11
<211> LENGTH: 494
<212> TYPE: PRT
<213> ORGANISM: Artificial Sequence
<220> FEATURE:
<221> NAME/KEY: SOURCE
<222> LOCATION: 1..494
<223> OTHER INFORMATION: /mol_type="protein"
      /note="TandAb D"
      /organism="Artificial Sequence"

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
            35                  40                  45

Ala Leu Ile Gly Gly Thr Asn Lys Arg Ala Pro Gly Val Pro Ser Arg
        50                  55                  60

Phe Ser Gly Ser Leu Ile Gly Asp Lys Ala Thr Leu Thr Ile Ser Ser
65                  70                  75                  80

```
Leu Gln Pro Glu Asp Phe Ala Thr Tyr Tyr Cys Ala Leu Trp Tyr Ser
                 85                  90                  95

Asn Leu Trp Val Phe Gly Gln Gly Thr Lys Val Glu Ile Lys Gly Gly
            100                 105                 110

Ser Gly Gly Ser Glu Val Gln Leu Val Gln Ser Gly Ala Glu Val Lys
        115                 120                 125

Lys Pro Gly Glu Ser Leu Lys Ile Ser Cys Lys Gly Ser Gly Tyr Ser
    130                 135                 140

Phe Thr Ser Tyr Trp Ile Gly Trp Val Arg Gln Met Pro Gly Lys Gly
145                 150                 155                 160

Leu Glu Trp Met Gly Ile Ile Tyr Pro Gly Asp Ser Asp Thr Arg Tyr
                165                 170                 175

Ser Pro Ser Phe Gln Gly Gln Val Thr Ile Ser Ala Asp Lys Ser Ile
            180                 185                 190

Ser Thr Ala Tyr Leu Gln Trp Ser Ser Leu Lys Ala Ser Asp Thr Ala
        195                 200                 205

Met Tyr Tyr Cys Ala Arg Leu Gly Ser Ser Trp Thr Asn Asp Ala Phe
    210                 215                 220

Asp Ile Trp Gly Gln Gly Thr Met Val Thr Val Ser Ser Gly Gly Ser
225                 230                 235                 240

Gly Gly Ser Ser Tyr Glu Leu Thr Gln Pro Pro Ser Val Ser Val Ser
                245                 250                 255

Pro Gly Gln Thr Ala Arg Ile Thr Cys Ser Gly Asp Ala Leu Pro Lys
            260                 265                 270

Gln Tyr Ala Tyr Trp Tyr Gln Gln Lys Pro Gly Gln Ala Pro Val Leu
        275                 280                 285

Val Ile Tyr Lys Asp Ser Glu Arg Pro Ser Gly Ile Pro Glu Arg Phe
    290                 295                 300

Ser Gly Ser Ser Ser Gly Thr Thr Val Thr Leu Thr Ile Ser Gly Val
305                 310                 315                 320

Gln Ala Glu Asp Glu Ala Asp Tyr Tyr Cys Gln Ser Ala Asp Ser Ser
                325                 330                 335

Gly Thr Pro Leu Ile Val Phe Gly Thr Gly Thr Lys Leu Thr Val Leu
            340                 345                 350

Gly Gly Ser Gly Gly Ser Glu Val Gln Leu Val Glu Ser Gly Gly Gly
        355                 360                 365

Leu Val Gln Pro Gly Gly Ser Leu Arg Leu Ser Cys Ala Ala Ser Gly
    370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
            420                 425                 430

Asp Asp Ser Lys Asn Ser Leu Tyr Leu Gln Met Asn Ser Leu Lys Thr
        435                 440                 445

Glu Asp Thr Ala Val Tyr Tyr Cys Ala Arg His Gly Asn Phe Gly Asn
    450                 455                 460

Ser Tyr Val Ser Tyr Phe Ala Tyr Trp Gly Gln Gly Thr Leu Val Thr
465                 470                 475                 480

Val Ser Ser Ala Ala Ala Gly Ser His His His His His
                485                 490
```

<210> SEQ ID NO 12
<211> LENGTH: 494
<212> TYPE: PRT
<213> ORGANISM: Artificial Sequence
<220> FEATURE:
<221> NAME/KEY: SOURCE
<222> LOCATION: 1..494
<223> OTHER INFORMATION: /mol_type="protein"
   /note="TandAb E"
   /organism="Artificial Sequence"

<400> SEQUENCE: 12

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Gly Leu Ile Gly Gly Thr Asn Lys Arg Ala Pro Gly Val Pro Ser Arg
    50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Glu Val Gln Leu Val Gln Ser Gly Ala Glu Val Lys
        115                 120                 125

Lys Pro Gly Glu Ser Leu Lys Ile Ser Cys Lys Gly Ser Gly Tyr Ser
    130                 135                 140

Phe Thr Ser Tyr Trp Ile Gly Trp Val Arg Gln Met Pro Gly Lys Gly
145                 150                 155                 160

Leu Glu Trp Met Gly Ile Ile Tyr Pro Gly Asp Ser Asp Thr Arg Tyr
                165                 170                 175

Ser Pro Ser Phe Gln Gly Gln Val Thr Ile Ser Ala Asp Lys Ser Ile
            180                 185                 190

Ser Thr Ala Tyr Leu Gln Trp Ser Ser Leu Lys Ala Ser Asp Thr Ala
        195                 200                 205

Met Tyr Tyr Cys Ala Arg Leu Gly Ser Ser Trp Thr Asn Asp Ala Phe
    210                 215                 220

Asp Ile Trp Gly Gln Gly Thr Met Val Thr Val Ser Ser Gly Gly Ser
225                 230                 235                 240

Gly Gly Ser Ser Tyr Glu Leu Thr Gln Pro Pro Ser Val Ser Val Ser
                245                 250                 255

Pro Gly Gln Thr Ala Arg Ile Thr Cys Ser Gly Asp Ala Leu Pro Lys
            260                 265                 270

Gln Tyr Ala Tyr Trp Tyr Gln Gln Lys Pro Gly Gln Ala Pro Val Leu
        275                 280                 285

Val Ile Tyr Lys Asp Ser Glu Arg Pro Ser Gly Ile Pro Glu Arg Phe
    290                 295                 300

Ser Gly Ser Ser Ser Gly Thr Thr Val Thr Leu Thr Ile Ser Gly Val
305                 310                 315                 320

Gln Ala Glu Asp Glu Ala Asp Tyr Tyr Cys Gln Ser Ala Asp Ser Ser
                325                 330                 335

Gly Thr Pro Leu Ile Val Phe Gly Thr Gly Thr Lys Leu Thr Val Leu
            340                 345                 350
```

-continued

Gly Gly Ser Gly Gly Ser Glu Val Gln Leu Val Glu Ser Gly Gly Gly
        355                 360                 365

Leu Val Gln Pro Gly Gly Ser Leu Arg Leu Ser Cys Ala Ala Ser Gly
    370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
            405                 410                 415

Ala Thr Tyr Tyr Ala Asp Ser Val Lys Asp Arg Phe Thr Ile Ser Arg
        420                 425                 430

Asp Asp Ser Lys Asn Ser Leu Tyr Leu Gln Met Asn Ser Leu Lys Thr
            435                 440                 445

Glu Asp Thr Ala Val Tyr Tyr Cys Ala Arg His Gly Asn Phe Gly Asn
450                 455                 460

Ser Tyr Val Ser His Phe Ala Tyr Trp Gly Gln Gly Thr Leu Val Thr
465                 470                 475                 480

Val Ser Ser Ala Ala Ala Gly Ser His His His His His
            485                 490

<210> SEQ ID NO 13
<211> LENGTH: 493
<212> TYPE: PRT
<213> ORGANISM: Artificial Sequence
<220> FEATURE:
<221> NAME/KEY: SOURCE
<222> LOCATION: 1..493
<223> OTHER INFORMATION: /mol_type="protein"
      /note="TandAb F"
      /organism="Artificial Sequence"

<400> SEQUENCE: 13

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu Gly Gly Ser
            100                 105                 110

Gly Gly Ser Glu Val Gln Leu Val Gln Ser Gly Ala Glu Val Lys Lys
        115                 120                 125

Pro Gly Glu Ser Leu Lys Ile Ser Cys Lys Gly Ser Gly Tyr Ser Phe
    130                 135                 140

Thr Ser Tyr Trp Ile Gly Trp Val Arg Gln Met Pro Gly Lys Gly Leu
145                 150                 155                 160

Glu Trp Met Gly Ile Ile Tyr Pro Gly Asp Ser Asp Thr Arg Tyr Ser
                165                 170                 175

Pro Ser Phe Gln Gly Gln Val Thr Ile Ser Ala Asp Lys Ser Ile Ser
            180                 185                 190

Thr Ala Tyr Leu Gln Trp Ser Ser Leu Lys Ala Ser Asp Thr Ala Met

```
            195                 200                 205
Tyr Tyr Cys Ala Arg Leu Gly Ser Ser Trp Thr Asn Asp Ala Phe Asp
    210                 215                 220

Ile Trp Gly Gln Gly Thr Met Val Thr Val Ser Ser Gly Gly Ser Gly
225                 230                 235                 240

Gly Ser Ser Tyr Glu Leu Thr Gln Pro Pro Ser Val Ser Val Ser Pro
                245                 250                 255

Gly Gln Thr Ala Arg Ile Thr Cys Ser Gly Asp Ala Leu Pro Lys Gln
                260                 265                 270

Tyr Ala Tyr Trp Tyr Gln Gln Lys Pro Gly Gln Ala Pro Val Leu Val
                275                 280                 285

Ile Tyr Lys Asp Ser Glu Arg Pro Ser Gly Ile Pro Glu Arg Phe Ser
        290                 295                 300

Gly Ser Ser Ser Gly Thr Thr Val Thr Leu Thr Ile Ser Gly Val Gln
305                 310                 315                 320

Ala Glu Asp Glu Ala Asp Tyr Tyr Cys Gln Ser Ala Asp Ser Ser Gly
                325                 330                 335

Thr Pro Leu Ile Val Phe Gly Thr Gly Thr Lys Leu Thr Val Leu Gly
                340                 345                 350

Gly Ser Gly Gly Ser Glu Val Gln Leu Val Glu Ser Gly Gly Gly Leu
        355                 360                 365

Val Gln Pro Lys Gly Ser Leu Lys Leu Ser Cys Ala Ala Ser Gly Phe
370                 375                 380

Thr Phe Asn Thr Tyr Ala Met Asn Trp Val Arg Gln Ala Pro Gly Lys
385                 390                 395                 400

Gly Leu Glu Trp Val Ala Arg Ile Arg Ser Lys Tyr Asn Asn Tyr Ala
                405                 410                 415

Thr Tyr Tyr Ala Asp Ser Val Lys Asp Arg Phe Thr Ile Ser Arg Asp
                420                 425                 430

Asp Ser Gln Ser Ile Leu Tyr Leu Gln Met Asn Asn Leu Lys Thr Glu
        435                 440                 445

Asp Thr Ala Met Tyr Tyr Cys Val Arg His Gly Asn Phe Gly Asn Ser
        450                 455                 460

Tyr Val Ser Trp Phe Ala Tyr Trp Gly Gln Gly Thr Leu Val Thr Val
465                 470                 475                 480

Ser Ser Ala Ala Ala Gly Ser His His His His His
                485                 490

<210> SEQ ID NO 14
<211> LENGTH: 494
<212> TYPE: PRT
<213> ORGANISM: Artificial Sequence
<220> FEATURE:
<221> NAME/KEY: SOURCE
<222> LOCATION: 1..494
<223> OTHER INFORMATION: /mol_type="protein"
      /note="TandAb G"
      /organism="Artificial Sequence"

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
                20                  25                  30

Ser Asn Tyr Ala Asn Trp Val Gln Gln Lys Pro Gly Lys Ala Pro Lys
        35                  40                  45
```

```
Gly Leu Ile Gly Gly Thr Asn Lys Arg Ala Pro Gly Val Pro Ser Arg
    50              55                  60
Phe Ser Gly Ser Leu Ile Gly Asp Lys Ala Thr Leu Thr Ile Ser Ser
65              70                  75                  80
Leu Gln Pro Glu Asp Phe Ala Thr Tyr Tyr Cys Ala Leu Trp Tyr Ser
                85                  90                  95
Asn Leu Trp Val Phe Gly Gln Gly Thr Lys Val Glu Ile Lys Gly Gly
            100                 105                 110
Ser Gly Gly Ser Glu Val Gln Leu Val Gln Ser Gly Ala Glu Val Lys
            115                 120                 125
Lys Pro Gly Glu Ser Leu Lys Ile Ser Cys Lys Gly Ser Gly Tyr Ser
    130                 135                 140
Phe Thr Ser Tyr Trp Ile Gly Trp Val Arg Gln Met Pro Gly Lys Gly
145                 150                 155                 160
Leu Glu Trp Met Gly Ile Ile Tyr Pro Gly Asp Ser Asp Thr Arg Tyr
                165                 170                 175
Ser Pro Ser Phe Gln Gly Gln Val Thr Ile Ser Ala Asp Lys Ser Ile
                180                 185                 190
Ser Thr Ala Tyr Leu Gln Trp Ser Ser Leu Lys Ala Ser Asp Thr Ala
            195                 200                 205
Met Tyr Tyr Cys Ala Arg Leu Gly Ser Ser Trp Thr Asn Asp Ala Phe
            210                 215                 220
Asp Ile Trp Gly Gln Gly Thr Met Val Thr Val Ser Ser Gly Gly Ser
225                 230                 235                 240
Gly Gly Ser Ser Tyr Glu Leu Thr Gln Pro Pro Ser Val Ser Val Ser
                245                 250                 255
Pro Gly Gln Thr Ala Arg Ile Thr Cys Ser Gly Asp Ala Leu Pro Lys
                260                 265                 270
Gln Tyr Ala Tyr Trp Tyr Gln Gln Lys Pro Gly Gln Ala Pro Val Leu
            275                 280                 285
Val Ile Tyr Lys Asp Ser Glu Arg Pro Ser Gly Ile Pro Glu Arg Phe
            290                 295                 300
Ser Gly Ser Ser Ser Gly Thr Thr Val Thr Leu Thr Ile Ser Gly Val
305                 310                 315                 320
Gln Ala Glu Asp Glu Ala Asp Tyr Tyr Cys Gln Ser Ala Asp Ser Ser
                325                 330                 335
Gly Thr Pro Leu Ile Val Phe Gly Thr Gly Thr Lys Leu Thr Val Leu
                340                 345                 350
Gly Gly Ser Gly Gly Ser Glu Val Gln Leu Val Glu Ser Gly Gly Gly
            355                 360                 365
Leu Val Gln Pro Gly Gly Ser Leu Arg Leu Ser Cys Ala Ala Ser Gly
    370                 375                 380
Phe Thr Phe Ser Thr Tyr Ala Met Asn Trp Val Arg Gln Ala Pro Gly
385                 390                 395                 400
Lys Gly Leu Glu Trp Val Gly Arg Ile Arg Ser Lys Tyr Asn Asn Tyr
                405                 410                 415
Ala Thr Tyr Tyr Ala Asp Ser Val Lys Asp Arg Phe Thr Ile Ser Arg
                420                 425                 430
Asp Asp Ser Lys Asn Ser Leu Tyr Leu Gln Met Asn Ser Leu Lys Thr
            435                 440                 445
Glu Asp Thr Ala Val Tyr Tyr Cys Ala Arg His Gly Asn Phe Gly Asn
    450                 455                 460
Ser Tyr Val Ser Trp Phe Ala Tyr Trp Gly Gln Gly Thr Leu Val Thr
```

```
                465                 470                 475                 480

Val Ser Ser Ala Ala Ala Gly Ser His His His His His
                            485                 490

<210> SEQ ID NO 15
<211> LENGTH: 494
<212> TYPE: PRT
<213> ORGANISM: Artificial Sequence
<220> FEATURE:
<221> NAME/KEY: SOURCE
<222> LOCATION: 1..494
<223> OTHER INFORMATION: /mol_type="protein"
      /note="TandAb H"
      /organism="Artificial Sequence"

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ser Thr Gly Ala Val Thr Thr
            20                  25                  30

Ser Asn Tyr Ala Asn Trp Val Gln Gln Lys Pro Gly Lys Ala Pro Lys
        35                  40                  45

Gly Leu Ile Gly Gly Thr Asn Lys Arg Ala Pro Gly Val Pro Ala Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Glu Val Gln Leu Val Gln Ser Gly Ala Glu Val Lys
        115                 120                 125

Lys Pro Gly Glu Ser Leu Lys Ile Ser Cys Lys Gly Ser Gly Tyr Ser
    130                 135                 140

Phe Thr Ser Tyr Trp Ile Gly Trp Val Arg Gln Met Pro Gly Lys Gly
145                 150                 155                 160

Leu Glu Trp Met Gly Ile Ile Tyr Pro Gly Asp Ser Asp Thr Arg Tyr
                165                 170                 175

Ser Pro Ser Phe Gln Gly Gln Val Thr Ile Ser Ala Asp Lys Ser Ile
            180                 185                 190

Ser Thr Ala Tyr Leu Gln Trp Ser Ser Leu Lys Ala Ser Asp Thr Ala
        195                 200                 205

Met Tyr Tyr Cys Ala Arg Leu Gly Ser Ser Trp Thr Asn Asp Ala Phe
    210                 215                 220

Asp Ile Trp Gly Gln Gly Thr Met Val Thr Val Ser Ser Gly Gly Ser
225                 230                 235                 240

Gly Gly Ser Ser Tyr Glu Leu Thr Gln Pro Pro Ser Val Ser Val Ser
                245                 250                 255

Pro Gly Gln Thr Ala Arg Ile Thr Cys Ser Gly Asp Ala Leu Pro Lys
            260                 265                 270

Gln Tyr Ala Tyr Trp Tyr Gln Gln Lys Pro Gly Gln Ala Pro Val Leu
        275                 280                 285

Val Ile Tyr Lys Asp Ser Glu Arg Pro Ser Gly Ile Pro Glu Arg Phe
    290                 295                 300

Ser Gly Ser Ser Ser Gly Thr Val Thr Leu Thr Ile Ser Gly Val
305                 310                 315                 320
```

-continued

```
Gln Ala Glu Asp Glu Ala Asp Tyr Tyr Cys Gln Ser Ala Asp Ser Ser
            325                 330                 335

Gly Thr Pro Leu Ile Val Phe Gly Thr Gly Thr Lys Leu Thr Val Leu
        340                 345                 350

Gly Gly Ser Gly Gly Ser Glu Val Gln Leu Val Glu Ser Gly Gly Gly
            355                 360                 365

Leu Val Gln Pro Gly Gly Ser Leu Arg Leu Ser Cys Ala Ala Ser Gly
        370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
            420                 425                 430

Asp Asp Ser Lys Asn Ser Leu Tyr Leu Gln Met Asn Ser Leu Lys Thr
        435                 440                 445

Glu Asp Thr Ala Val Tyr Tyr Cys Ala Arg His Gly Asn Phe Gly Asn
    450                 455                 460

Ser Tyr Val Ser Trp Phe Ala Tyr Trp Gly Gln Gly Thr Leu Val Thr
465                 470                 475                 480

Val Ser Ser Ala Ala Ala Gly Ser His His His His His His
                485                 490
```

<210> SEQ ID NO 16
<211> LENGTH: 6
<212> TYPE: PRT
<213> ORGANISM: Artificial Sequence
<220> FEATURE:
<221> NAME/KEY: SOURCE
<222> LOCATION: 1..6
<223> OTHER INFORMATION: /mol_type="protein"
      /note="peptide linker"
      /organism="Artificial Sequence"

<400> SEQUENCE: 16

```
Gly Gly Ser Gly Gly Ser
1               5
```

<210> SEQ ID NO 17
<211> LENGTH: 4
<212> TYPE: PRT
<213> ORGANISM: Artificial Sequence
<220> FEATURE:
<221> NAME/KEY: SOURCE
<222> LOCATION: 1..4
<223> OTHER INFORMATION: /mol_type="protein"
      /note="peptide linker"
      /organism="Artificial Sequence"

<400> SEQUENCE: 17

```
Gly Gly Ser Gly
1
```

<210> SEQ ID NO 18
<211> LENGTH: 5
<212> TYPE: PRT
<213> ORGANISM: Artificial Sequence
<220> FEATURE:
<221> NAME/KEY: SOURCE
<222> LOCATION: 1..5
<223> OTHER INFORMATION: /mol_type="protein"
      /note="peptide linker"
      /organism="Artificial Sequence"

```
<400> SEQUENCE: 18

Gly Gly Ser Gly Gly
1               5
```